(12) United States Patent
Zulf

(10) Patent No.: US 7,774,254 B2
(45) Date of Patent: Aug. 10, 2010

(54) SYSTEM FOR STORING VITAL RECORDS

(75) Inventor: Nara Zulf, Bethesda, MD (US)

(73) Assignee: Alec Zulf, Bethesda, MD (US)

( * ) Notice: Subject to any disclaimer, the term of this patent is extended or adjusted under 35 U.S.C. 154(b) by 0 days.

(21) Appl. No.: 12/038,615

(22) Filed: Feb. 27, 2008

(65) Prior Publication Data

US 2009/0216672 A1   Aug. 27, 2009

(51) Int. Cl.
*G06Q 99/00* (2006.01)
(52) U.S. Cl. ....................................................... 705/35
(58) Field of Classification Search ................... 283/70; 348/51; 702/1; 705/3, 35, 404, 65, 67; 713/182, 713/202; 707/1; 726/27, 30
See application file for complete search history.

(56) References Cited

U.S. PATENT DOCUMENTS

| | | | | |
|---|---|---|---|---|
| 7,003,669 | B2 * | 2/2006 | Monk | 713/182 |
| 7,375,862 | B2 * | 5/2008 | Tu | 358/474 |
| 2004/0059953 | A1 * | 3/2004 | Purnell | 713/202 |
| 2004/0196362 | A1 * | 10/2004 | Hoshino et al. | 348/51 |
| 2006/0109498 | A1 * | 5/2006 | Ferlitsch | 358/1.15 |
| 2006/0256371 | A1 * | 11/2006 | King et al. | 358/1.15 |
| 2007/0220614 | A1 * | 9/2007 | Ellis et al. | 726/27 |
| 2008/0235175 | A1 * | 9/2008 | Olive | 707/1 |
| 2009/0025092 | A1 * | 1/2009 | Smith et al. | 726/30 |

OTHER PUBLICATIONS

Real Time Privilege Management, Assuretec Systems Inc, Mar. 26, 2004.*
System and Method Relating to Remotely Accessible Securely Stored Data Files, Original Spin (International) PTY Ltd, Nov. 14, 2002.*
Document and Bearer Verification System, Assuretec Systems Inc, Dec. 17, 2001.*

* cited by examiner

*Primary Examiner*—James P Trammell
*Assistant Examiner*—Tien C Nguyen
(74) *Attorney, Agent, or Firm*—Michael L. Greenberg, Esq.; Greenberg & Lieberman, LLC

(57) ABSTRACT

A system for storing vital personal and business records in one secure location. A user may create an account and submit documents to be scanned and uploaded through a public kiosk. Documents may include, but are not limited to, such items as driver's licenses, birth certificates, state and federal identification cards and health information. The information is transmitted to a secure server where it is stored. A user may then utilize a computing device via secure online means to gain access to his or her stored documents.

16 Claims, 3 Drawing Sheets

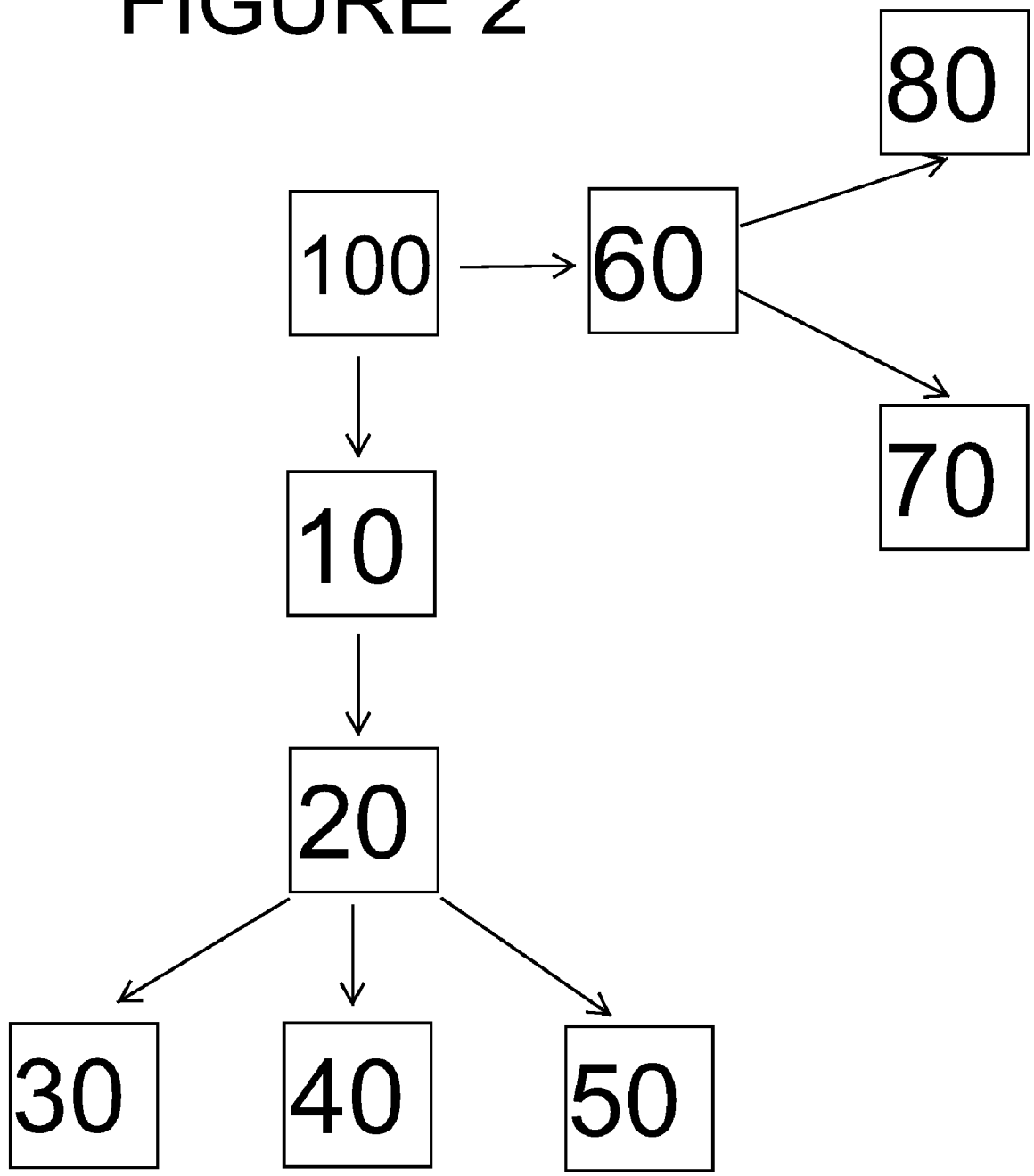

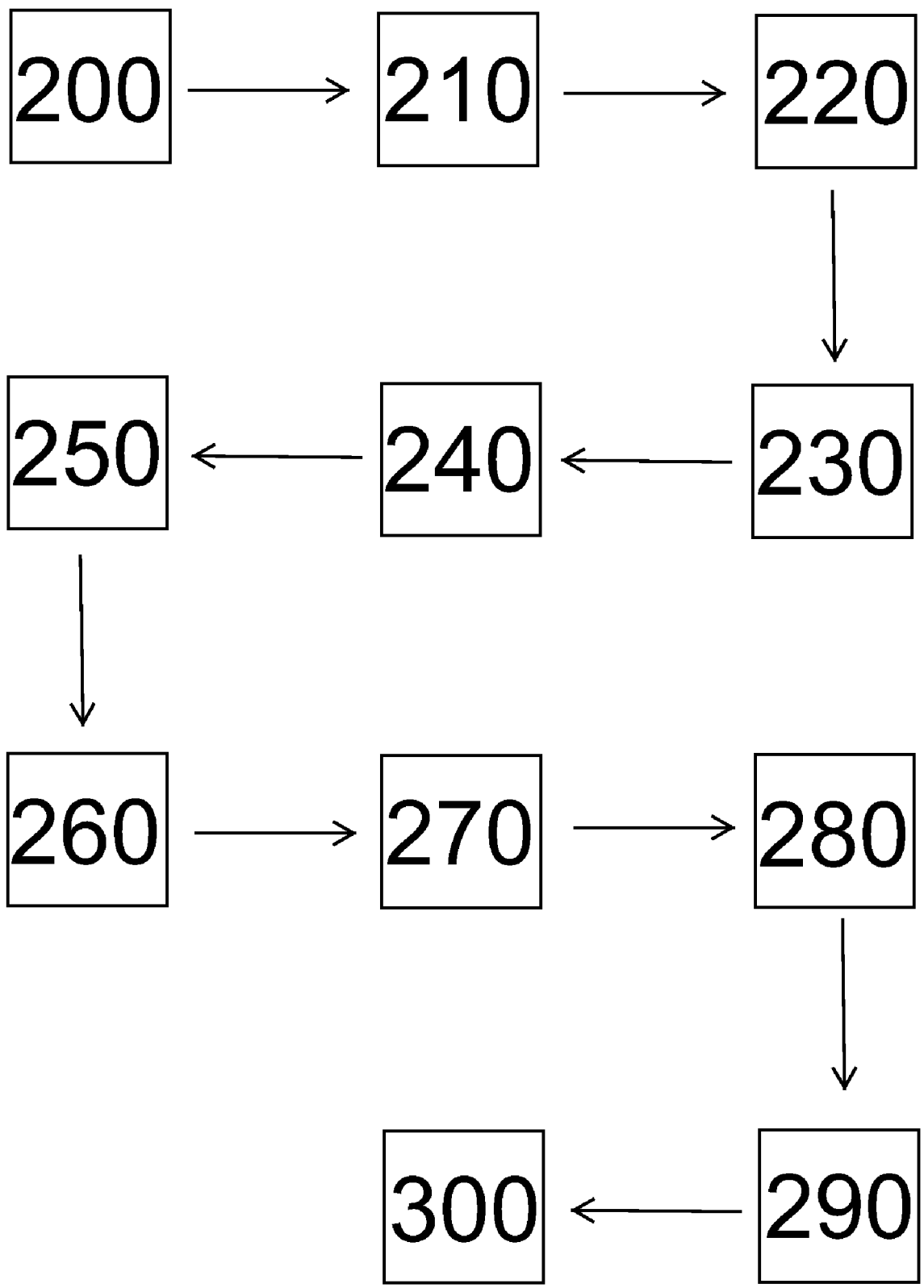

SYSTEM FOR STORING VITAL RECORDS

FIELD OF THE INVENTION

The present invention is a system for the consolidated storing and convenient retrieval of important documents, particularly vital personal records. The system is comprised of a kiosk, a secure network, a secure server, and related software that work to permit a user to securely scan high-resolution copies of various vital documents at a kiosk terminal, which would then work through the system to ultimately store encrypted and password-protected versions of these documents for easy retrieval if necessary.

BACKGROUND OF THE INVENTION

A person's legal identity is a precious item. Often, an identity is manifested in the form of various vital documents. This includes birth certificates, drivers' licenses, passports, insurance cards, residency cards, social security cards and military identification. Many of these items are difficult to replace. In addition, these types of vital documents also are often needed to prove an identity in order to receive replacement documentation or otherwise prove identity. This issue becomes an extraordinary problem when an unexpected disaster falls upon an individual.

For example, a fire that destroys a home may very well ruin all of a person's belongings, including vital documents. After such a tragedy, that person would have the additional hassle of replacing such documents within a scenario where he or she may not even have a wallet left to prove their actual identity to a government official. This often results in hours—if not days or weeks—of hassle and bureaucracy in the midst of a tragedy. Moreover, this situation is not limited to fires. Natural disasters such as tornados, hurricanes and floods all have resulted in complete destruction of documents. While such protective items as fireproof safes are helpful in protecting vital documents, even these types of protective measures either are not completely secure or are exceptionally expensive for average consumers. A person in this situation would also have difficulty retrieving these documents in an outside safety deposit box because in order to access or seek a new key to many of these boxes, a proper identification is required. Because of these facts, there is a need for a system that provides easy access to high-quality versions of these vital records.

Disasters at home also are not the only tragedies that can affect vital documents. For example, travelers in some foreign countries may lose their passport. Or a domestic traveler may lose his or her wallet and all of its identification. When these circumstances occur, it is increasingly difficult for a traveler to do much of anything, let alone seek shelter, food or travel home. The reason, again, is that the person would not have any sort of identification needed to access various options toward bettering the situation or recouping funds. This scenario further highlights the need for a system that provides easy access to high-quality versions of vital identification documents.

Beyond the tragic and helpless scenarios, it is also a wise decision to safely store high-quality copies of vital records in a secure and completely protected medium. People are often asked to present copies of their social security card or birth certificate. But when they lose their originals or copies in hand, these people must navigate through the bureaucracy, fill out forms and wait in long lines. And that will be successful only if they have other identification documents. This issue can be even more urgent for a person seeking to replace a green card. From this, it is clear that a need exists for a system to allow users to scan high-resolution copies of their vital documents into a secure server, where all they would need to do is enter a password and/or other personal information to retrieve high quality printed copies on demand. The present invention satisfies this need by establishing a system where people can utilize a kiosk to place these vital documents in an encrypted server for later retrieval on demand. The present invention applies security measures at all levels of the system to ensure safe identity protection. The present invention is needed because it provides one secure location for the storage of personal or business documents.

The present invention is unique and solves many problems—both real and potential—relating to the storage of vital document images. For example, it is quite common for people to send themselves an email with an attachment of a document they scanned themselves. However, this method is not completely secure as it is well documented that users with accounts on such areas as YAHOO!™ and HOTMAIL™ sometimes find that all documents have been purged. These and other electronic storage options also fail to achieve the speed and security elements that are prevalent with the present invention. For example, an emailed attachment to a current consumer server is not prefaced and veiled in all-encompassing security, as is the present invention. An onlooker conceivably can watch a user at a traditional computer type in his or her password in order to eventually comprise the security of the files. The user also has more hoops to jump through with less assurance of security in contrast to the speedy aspects of the present invention.

Even so-called secure storage servers such as the military "IPERMS" system is flawed in terms of user friendly speed and conciseness. With "IPERMS", a service member must submit his or her military records through a chain of command and civilian bureaucracy at the unit level, where the documents are scanned through a military network and forwarded to a human resources attendant. That human resources attendant then plugs the same scanned image of military records into the "IPERMS" system where a service member may retrieve the images via online connection. While "IPERMS" operates through a secure server, the user must still retrieve these documents via an online connection. This entails entering a military ID card into a Web site sometimes called "Army Knowledge Online" or "Defense Knowledge Online." From that Web site, the user must then click onto "IPERMS" and type in a password and username again. From there, a confusing list of documents with arbitrary listings awaits the user in a tedious and time-consuming manner. The present invention, in contrast, actually offers increased overall security over the documents while lessening the time and energy involved in comparison to "IPERMS" and similar storage items. In addition, the present invention offers the user an opportunity to review his or her documents to ensure the highest quality scan, whereas other items such as "IPERMS" are not known for quality images. Also, systems such as "IPERMS" take the control of the documents submitted out of the hands of the user, because with "IPERMS," third and often fourth parties must take control and decide what is stored. In the present invention, the user controls what information and how much information is stored without dealing through additional people.

Another difference between the present invention and scanning personal documents on a traditional business scanner is that these business machines potentially may archive a record of this document. This causes significant security issues for the user wishing to store images of his or her vital records. The present invention, in contrast, protects the user by permitting him or her a completely secure avenue for storing vital documents. A similar issue relates to scanners at commercial outlets as well. Moreover, home scanners are not secure and susceptible to interception via wired or wireless routers. In addition, images that are scanned from a home scanner will either be stored on a disk or hard drive that potentially can be damaged or fail. The present invention, meanwhile, deploys secure kiosks at designated public locations such as banks, post offices, libraries, office courtyards, doctors' offices, hospitals and veterinary offices. These kiosks permit users to immediately receive vital documents and quickly and securely upload their images into the secure server of the present invention.

Unlike conventional email and server systems such as "IPERMS," the present invention spares the user of the need to type and label information relating to the item to be scanned. Instead, a user of the present invention merely pushes pre-designated buttons at a kiosk, which has the additional veil of security through the use of a display screen that only a user looking straight ahead may view its contents.

SUMMARY OF THE INVENTION

The present invention is a system for storing and easily retrieving important documents, particularly vital documents relating to a person's identity. Images of these documents are effectively stored in a single location through the use of a secure server operated via conventional means. The system of the present invention includes a kiosk capable of scanning and transmitting these documents in a private, secure and high-quality manner. Once the document is received by the image-scanning device in digital image format, the information is immediately compressed and encrypted via conventional means. Software helps drive the function of the kiosk image capturing elements, as well as the encryption and transmission process. The information is then transmitted via conventional means to a secure server where it is stored. An individual may then utilize a security mechanism such as a personalized password at a secure Web site in order to retrieve high-quality images of these documents. It should be noted that once the data is successfully transmitted from the kiosk to the secure server, this information is immediately deleted from the kiosk. This means that there will be no trace within the kiosk memory of the actual documentation that had been uploaded. The preferred embodiment of the present invention includes this element to avoid security and privacy issues that have plagued certain copy machines relating to retained memory of scanned items hidden deep in its system. However, an embodiment of the present invention initiates this deletion process when the kiosk receives final verification that the information was successfully uploaded without errors. The deletion process in the preferred embodiment is controlled by a separate software function that can save within the kiosk any information subjected to uploading errors until the transmission is ultimately verified, at which point the information will then be permanently deleted from the kiosk.

In an additional embodiment of the present invention, a user also may use enabled security features from a secure Web site in order to upload or otherwise access their personal documents. The secure server, meanwhile, is capable of storing a substantial amount of data. The secure server also is comprised of conventional means in terms of handling relatively high amounts of user activity. Kiosk and server operating software also are of conventional means.

BRIEF DESCRIPTION OF THE DRAWINGS

FIG. 2 is a flow chart detailing the preferred embodiment of the online retrieval method of the system.

FIG. 3 is a flow chart detailing the procedures of the system in its preferred embodiment.

DETAILED DESCRIPTION OF THE PREFERRED EMBODIMENT

Figure 1:
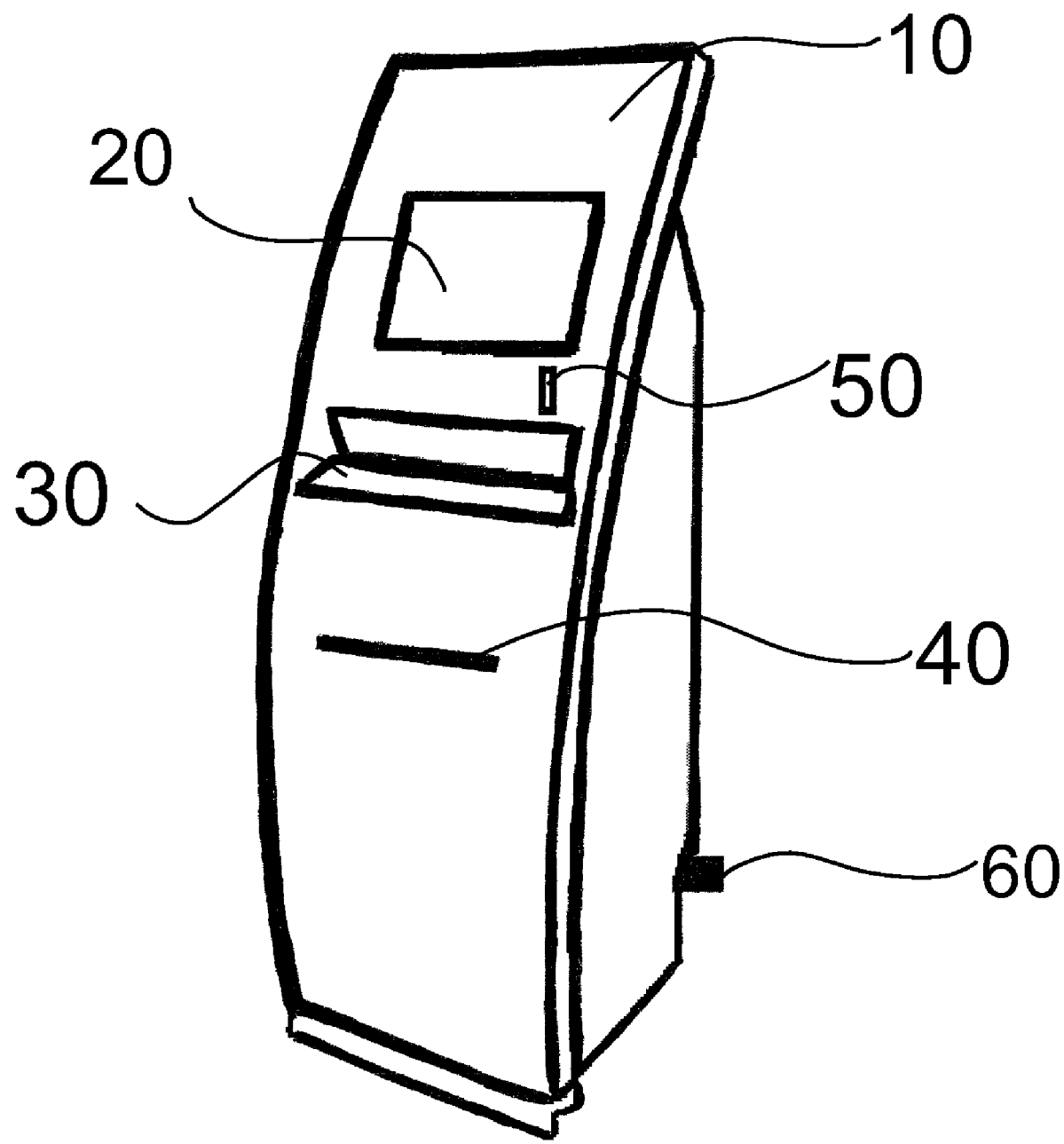
FIG. 1 is a view of a kiosk of the preferred embodiment of the present invention

In FIG. 1, we see the preferred embodiment of the system pertaining to the kiosk. It is envisioned that various kiosks will be located at select public locations. This is similar to the dispersion of such secure—physically and electronically—items as automatic-teller machines. The example of FIG. 1 shows how the kiosk will include a kiosk casing (10). The kiosk casing (10) is the housing of this aspect of the present invention. Much of the internal elements housed inside the kiosk casing (10) operate via conventional means, which also requires protection from such items as weather and vandalism.

A display screen (20) operates so that the user may visually review his or her options. In the preferred embodiment of the present invention, the display screen (20) can only be viewed by the user looking straight ahead toward the display screen (20). This security element prevents others who may be standing off to the side or at higher elevations above from viewing the contents of the display screen (20). An additional element of the preferred embodiment includes touch screen technology on the display screen (20) for easy use. Information gleaned from the display screen (20) include instructions for use of the system, as well as document review so that the user may view the quality of the document after it is uploaded.

While the preferred embodiment includes touch screen technology, FIG. 1 displays an embodiment that includes a keypad (30). The keypad (30) may be a more traditional keyboard or digital. The keypad (30) allows the user to type in the relevant information relating to his or her personal information and billing preferences. The keypad (30) also permits the user to type in a unique username and password, as well as other security information that will be useful during the data retrieval process. Prompts displayed on the display screen (20) guide the user, as the information is stored with other elements of the user's file at the secure server. It should be noted that the keypad (30) is merely an embodiment as most or all of the actual decisions can be made via the display screen (20).

In the embodiment of FIG. 1, we also see an opening for an image-scanning device (40). The image-scanning device (40) is of high quality and conventional in nature. The image-scanning device (40) is capable of adjusting itself to fit the varying dimensions of documents to be scanned. The image-scanning device (40) also adapts to ensure a proper scan of the differing variety of documents such as social security cards, driver's licenses, identification cards, birth certificates, health insurance cards and pages of passports. After a document is scanned by the image-scanning device (40), the user may simply remove the document from the kiosk. A billing element (50) such as a credit card reader also may be included as seen in FIG. 1. The billing element (50) operates in conjunction with the images displayed on the display screen (20) and keypad (30). Billing data also will ultimately travel within the server connection (60) to the server to be included with the user's personal information that is stored in that aspect of the present system.

Conventional elements within the kiosk casing (10) operate to convert the scanned image of the document into digital or otherwise appropriate conventional format for enhanced storage and transmission. From there, the information is immediately compressed and encrypted via conventional means. Software helps drive the function of the kiosk image capturing elements, as well as the encryption and transmission process. Once the data is successfully transmitted from the kiosk, this information is immediately deleted. In that way, there is no trace of the user's billing information or images of that user's scanned documents within the confines of the kiosk. Instead, all information is transmitted to a secure server via a conventional server connection (60). In FIG. 1, we see that the server connection (60) is manifested as a hardwire link through the standard network. It is conceived, however, a secure wireless connection also is plausible.

The kiosk in the preferred embodiment is deployed to designated public locations such as—but not limited to—banks, post offices, libraries, government buildings, office courtyards, doctors' offices, hospitals and veterinary offices. This ultimately creates a network of kiosks used to upload the images and the user information to the secure server. These kiosks permit users who had recently received a vital document to quickly and securely upload their images into the secure server of the present invention via the kiosk. Because the kiosks are deployed to various strategic locations, the user will not have to rely on other people to physically handle the documents for storage. In addition, the user will engage in uploading and scanning the vital document through the kiosk's secure connection to the secure server, along with the user-only viewing element of the display screen (20) and interactive, typing-free aspects of the display screen (20). From this, the kiosk and kiosk deployment is important because it spares the user from scanning vital documents using home or traditional public or office scanners.

The kiosk is used to transmit and ultimately store as many documents as the user desires within the confines of preselected storage plans into one secure server. In the preferred embodiment of the present invention, users employing the system will engage in varying storage plans. For example, a user with only a small amount of documents may elect to pay less amount of money for a lower tier program, which will limit the amount of information that can be stored in the secure server. Meanwhile, a higher tier program would cost a user more money but would allow him or her to store more information within the secure server. Once this information is stored in the secure server, however, the system of the present invention provides avenues for the user to easily and securely retrieve this information. In FIG. 2, we see a flow chart of the present invention relating to the online retrieval method. In the embodiment of FIG. 2, we see the security steps taken as a user logs into a retrieval device, which may be a computing device attached to a secure network.

When a user wishes to retrieve documents stored within the secure server, he or she will log onto the secure Web site associated with the system. In the preferred embodiment, the initial login screen (100) will ask the user to enter a username and password. The user will have the option to enter the username and password information or click on a link for those who may have forgotten or otherwise lost this information. If the user correctly enters the relevant user information in the initial login screen (100), he or she will reach a welcome screen (110). At the welcome screen (110), the user will have the option to click on a link and retrieve a digital image of a specific document that had been uploaded into the secure server at a previous time. For example, a user's file stored within the secure server may include a driver's license, social security card and birth certificate. In this example, the welcome screen (110) will include links to "driver's license," "social security card," and "birth certificate." The user may then choose and click on the desired link.

An additional way is described as to describing the enhanced security aspect relating to how Web retrieval access operates in conjunction with individuals who have scanned pertinent data via the kiosk. When a user accesses the Web, prior to viewing, the user will have to undergo a registration process again for security purposes (similar to online banking double or triple protection) and upon successful registration be forwarded to an area for kiosk users where he or she will have to use user name and password set up at the kiosk. This double vault process ensures enhanced security for user's protection.

Once a user clicks on a specific link, he or she will then be taken to a viewing page (120). At this page, the user will see the digital image of the document that had previously been scanned and uploaded into the secure server. In the preferred embodiment of the viewing page (120), the user will have the option to print the document (130), download and view document (140) in the file or log out (150). The print the document (130) option permits a printer friendly copy of the original scanned image to be printed and taken away by the user. Once the user has viewed and/or printed any documents, he or she may log out (150) in a secure manner.

While the above information relates to the online retrieval element of the present invention, FIG. 2 also provides flow chart information involving a forgotten or lost password. Going back to the initial login screen (100), a forgot password link sits next to the traditional enter link in the preferred embodiment. The forgot password link takes the user to a forgot password screen (160). The forgot password screen (160) presents the user with questions relating to information that was entered into the kiosk and stored within the secure server. Generally, the preferred embodiment of the present invention envisions two sets of security questions and answers to correspond with a username. It is conceived that additional technology such as portable retinal or fingerprint scans, along with conventional facial recognition technology used to take pictures at the kiosk and ultimately be used to compare photographs in lieu of other security measures during the online retrieval process may supplant this aspect of the system, but it remains in light of existing technology that the more traditional username/password/security questions are the preferred embodiment.

Once the required information is entered on the forgot password screen (160), the user may click onto a retrieve password link (170). The forgot password screen (160) also provides the option for the user who failed to remember the security question information to call a telephone number (180) where a customer service representative can aid in the process. A password change option (190) also is available.

FIG. 3 is an additional flow chart that details the steps a user of the system would go through. First, the user will arrive at a kiosk (200). The user will approach the kiosk and will be greeted by the display screen (20). Through the visual prompts of the display screen (20) and keypad (30), the user will create an account (210). This account will include a username, password, security questions and security answers. Typically, users will enter their first name and last name at a registration screen on the display screen (20). However, the system will automatically generate first initial and last name sequences of which the user will be informed.

The purpose of this embodiment is to promote simplistic recall of the username. An example of this embodiment would be "jsmith." It is conceived that unique identifiers will be searched by the overall system to distinguish between such examples of multiple "John Smiths." It is envisioned that a printing or receipt may be available for the user.

Additional information such as address, telephone number and other identifiers must be entered. In addition, the user will then enter into a storage space plan (220). At this point, the user may swipe a credit card into the billing element (50) or utilize a secure online transaction so long as it is routed through a separate secure server. Various billing options will be available to the user in the preferred embodiment. This includes different storage packages relating to the number and size of documents, as well as trial periods and other ventures.

Once the user enters into a storage plan (220), he or she may then start scanning documents (230). In the preferred embodiment, documents are placed into the image-scanning device (40) face down and covered for additional protection. These documents may be personal records, business records or virtually any type of documentation desired by the user to be preserved in one secure location. The user has an opportunity to view the digital image of the document before final transmission. Once the user starts scanning documents (230), or otherwise finishes processing, the digital information is securely transmitted to the secure server (240) where it is stored and protected. Immediately, this information is deleted (250) from the all parts of the kiosk. It is important to note that when this information is deleted (250), it is only deleted upon successful transmission of the relevant information. From this point, the user can only access his or her personal information and data through a computer and secure network.

This is the beginning of the retrieval process as the user logs onto a secure computer (260). The user then logs into the system (270). This begins the process as detailed in FIG. 2. After a successful login, the user will view a desired document (280) that is stored in the secure server. The secure server is conventional in nature and capable of holding vast amounts of storage. The user then may print the document (290). Finally, the user will log out (300).

It should be recognized that the present invention is particularly suited to speeding up the uploading and secure storage process. This is essential for the time-pressed user who wishes to upload his or her vital documents into a secure kiosk environment and ultimately to store these vital documents in encrypted form at the secure server as is done with the present invention. Because of limited time factors related to consumers, the present invention is configured to allow users to set up various storage plans that best meet the needs of the user. For example, although the kiosk includes a keypad (30), the system of the present invention provides the ability to avoid typing in the conventional sense of using a keypad (30) and instead defers most interactive functions to pressing digital images on the display screen (20). In this embodiment, a user will be offered the opportunity to choose from a list of documents that are listed on the display screen (20) of the kiosk. In this embodiment, the user will approach the kiosk and choose a language preference. Then the user of this embodiment will view various document storage plans on the display screen (20). For example, a basic plan might offer a listing of four vital documents to be stored within the system at a lower tier cost to the user. The display screen (20) also will provide the user with additional expanded offers that cost more money, but also offer more documents to be stored. One example relating to an expanded program listing would be a listing of 10 documents, where the user may choose six to be scanned, uploaded and stored within the system. The speed aspect relating to the new or expanded user accounts in this embodiment envision individual buttons that represent specific types of documents. These buttons of this embodiment can be physical buttons, but in the preferred aspect of this embodiment, the buttons will be digital operating in conjunction via conventional means with the display screen (20). So if a user presses the button for a social security card, the system will then be informed that the next item to be scanned and uploaded is the social security card. The system will then engage in the aforementioned computing and cataloguing via conventional means to compress the information, encrypt the information, pass this information through the system to the secure server using conventional security protocols and ultimately encrypt the appropriate database fields for enhanced security.

This embodiment is important for speed purposes as it guides the user along based on the desires and secure storage needs of each user. Moreover, the function of the present invention to choose buttons representing various items is much quicker and also better secure. While the kiosk display screen (20) is configured via conventional means to be viewed by the user looking straight ahead into the display screen (20), the present invention avoids typing because onlookers can monitor typing as well. Therefore, a user choosing pre-set options that are simple and concise while also in digital button form offers an additional level of security to accompany the increased speed of use.

Speed and simplicity for the user also includes the embodiment of placing sample pictures of the document next to its corresponding button so that the user has a visual identifier, as well as text, to help minimize user confusion. It should be recognized that icon recognition, or buttons, work to alleviate potential security breaches during option selection amidst desired high security. In essence, it should be recognized that security is less reliable if a user must name his or her own documents due to potential onlookers and various evidence factors on the keypad (30) such as dirt. The security concern aspect means that the present invention's use of having the user pre-select what is going to be scanned as opposed to naming afterwards benefits the overall privacy for the user. Also, the present invention permits the user to add in documents that are sequentially numbered according to the category selected.

By choosing various storage plans and prelisted documents, the user will not have to expend time and energy listing the document because the system will have done it already. If a mistake is made, the system provides the user with the opportunity to correct that mistake through scanning previews and other mistake cancellation means via conventional elements. Along these same lines, the retrieval aspect of this embodiment of the present invention correlates with the input aspect. In this embodiment, a user will go to the secure Web site, whether it is at home, government office, etc, and click on the program that they had chosen through the above online retrieval element of the system. However, in this embodiment, a screen using security protocols will feature hyper links showing the pre-programmed listing and perhaps a thumbnail image of the documents on file. From this point, the user may retrieve the document.

Other security measures also are important to mention in that these elements of the present invention permit quick resolution to forgotten passwords and identifiers when retrieving the uploaded vital document images from the secure server. These elements also are more secure, particularly for the user desiring to store his or her vital document images in encrypted form within the secure server. Going back to the kiosk in this embodiment, the kiosk also may have a camera secured to the kiosk casing (10). Other image memory items operating via conventional means such as facial, fingerprint and retinal recognition programs also are considered. In this embodiment, a user who may have forgotten his or her password may go back to a kiosk and simply get recognized through one or more of these recognition programs where the user may then engage in the process of changing his or her password and other security information.

The embodiment relating to the functionality of the kiosk also involves issuing a receipt and printed instructions after the user's session is ended. This also includes an on-screen notification that the transaction is successfully completed. Automated communications processes within the overall system also operate via conventional means in this additional embodiment. In that respect, the system will issue automated emails, regular mailings and/or text messages to users conveying such information as expiring accounts, attempted logins and account renewal information. It is important to note that keeping the user informed of the status and security elements of the vital document images within the secure server offers numerous intangibles such as piece of mind. This is important because a user within the system of the present invention stores these document images in the secure server that is monitored and protected from catastrophes that sometimes hit other document storage items such as sudden loss of all emails when a person "e-mail's it to himself" and other electronic storage device crashes.

Having illustrated the present invention, it should be understood that various adjustments and versions might be implemented without venturing away from the essence of the present invention. The present invention is not limited to the embodiments described above, and should be interpreted as any and all embodiments within the scope of the following claims.

I claim

1. A system for storing vital records, comprising:
scanning images via a kiosk;
creating a new user account with new billing information upon each visit to the kiosk;
associating the user information with the images;
accepting payment from the user;
preventing onlookers, at different viewing angles from the user, from viewing the user information and the images on a display screen in communication with the kiosk, the display screen configured to only allow the user looking straight ahead at the display screen and actively using the kiosk to view contents on the display screen;
reviewing the user information and the images on the display screen;
pre-selecting the user information and the images to be scanned prior to scanning;
uploading the images and the user information to a secure server, with the user pushing a pre-designated button and not typing and labeling the images to be scanned;
deleting the images, the images having been scanned by the user at the kiosk, and the user information automatically from the kiosk;
routing personal information through a separate secure server;
retaining the images and the user information on the secure server such that the images and the user information retained on the secure server are each stored together and confined to a pre-selected storage plan;
providing online links to the images and the user information that is retained on the secure server such that the images and the user information that is retained on the secure server can be viewed while being stored;
retrieving the images and the user information stored in the secure server from a device other than the kiosk;
preventing downloading at the kiosk; and
only accessing a username and password of the user through a computer and secure network, but not the kiosk.

2. The system for storing vital records of claim 1, wherein said scanning images via the kiosk captures the images in digital format.

3. The system for storing vital records of claim 1, further comprising creating an account for the user and establishing user identification information based upon said accepting user information from the user.

4. The system for storing vital records of claim 1, further comprising creating an account for the user, the account having a storage plan, the account based upon said associating the user information with the images.

5. The system for storing vital records of claim 1, wherein said accepting payment from the user allows said uploading the images and the user information to a secure server, said uploading the images and the user information to a secure server based upon a storage plan chosen by the user.

6. The system of storing vital records of claim 1, wherein said preventing onlookers from viewing the user information and the images is achieved by using the display screen that can only be viewed by the user.

7. The system for storing vital records of claim 6, wherein said display screen is interactive.

8. The system for storing vital records of claim 1, wherein said reviewing the user information and the images is displayed on the display screen for final acceptance by the user.

9. The system of storing vital records of claim 1, wherein said uploading the images and the user information to a secure server is transferred in a secure format.

10. The system of storing vital records of claim 1, wherein said deleting the images and the user information from the kiosk erases all memory of the images and the user information from the kiosk after the user information and the images are successfully uploaded to the secure server.

11. The system of storing vital records of claim 1, wherein said retaining the images and the user information on the secure server is accessing the images and the user information via only methods other than email.

12. The system of storing vital records of claim 1, wherein said retrieving the images and the user information stored in the secure server is downloading via online access.

13. The system of storing vital records of claim 12, wherein said retrieving the images and the user information stored in the secure server is retrieving the images and the user through affirmative validation based on the personal identification information.

14. The system for storing vital information of claim 1, further comprising configuring a network of kiosks to upload the images and the user information to the secure server.

15. A system for storing vital records, comprising:
scanning images via a kiosk;
creating a new user account with new billing information upon each visit to the kiosk;
associating the user information with the images;
accepting payment from the user;
preventing onlookers, at different viewing angles from the user, from viewing the user information and the images on a display screen in communication with the kiosk, the display screen configured to only allow the user looking straight ahead at the display screen and actively using the kiosk to view contents on the display screen;

reviewing the user information and the images on a display screen;

pre-selecting the user information and the images to be scanned prior to scanning;

uploading the images and the user information to a secure server, with the user pushing a pre-designated button and not typing and labeling the images to be scanned;

deleting the images, the images having been scanned by the user at the kiosk, and the user information automatically from the kiosk;

routing personal information through a separate secure server;

retaining the images and the user information on the secure server such that the images and the user information retained on the secure server are each stored together and confined to a pre-selected storage plan;

providing online links to the images and the user information that is retained on the secure server such that the images and the user information that is retained on the secure server can be viewed while being stored;

retrieving the images and the user information stored in the secure server from a device other than the kiosk;

preventing downloading at the kiosk; and only accessing a username and password of the user through a computer and secure network, but not the kiosk;

wherein said scanning images via a kiosk captures the images in digital format;

wherein said creating an account for the user and establishing user identification information based upon said accepting user information from the user;

wherein said creating an account for the user, the account having a storage plan, the account based upon said associating the user information with the images;

wherein said accepting payment from the user allows said uploading the images and the user information to a secure server, said uploading the images and the user information to a secure server based upon a storage plan chosen by the user;

wherein said preventing onlookers from viewing the user information and the images is achieved by using the display screen that can only be viewed by the user;

wherein said display screen is interactive;

wherein said reviewing the user information and the images is displayed on the display screen for final acceptance by the user;

wherein said uploading the images and the user information to a secure server is transferred in a secure format;

wherein said deleting the images and the user information from the kiosk erases all memory of the images and the user information from the kiosk after the user information and the images are successfully uploaded to the secure server;

wherein said retaining the images and the user information on the secure server is accessing the images and the user information via only methods other than email;

wherein said retrieving the images and the user information stored in the secure server is downloading via online access; and wherein said retrieving the images and the user information stored in the secure server is retrieving the images and the user through affirmative validation based on the personal identification information.

16. A system for storing vital records, comprising:

scanning images via a kiosk;

creating a new user account with new billing information upon each visit to the kiosk;

associating the user information with the images;

accepting payment from the user;

preventing onlookers, at different viewing angles from the user, from viewing the user information and the images on a display screen in communication with the kiosk, the display screen configured to only allow the user looking straight ahead at the display screen and actively using the kiosk to view contents on the display screen;

reviewing the user information and the images;

pre-selecting the user information and the images to be scanned prior to scanning;

uploading the images and the user information to a secure server, with the user pushing a pre-designated button and not typing and labeling the images to be scanned;

deleting the images, the images having been scanned by the user at the kiosk, and the user information automatically from the kiosk;

routing personal information through a separate secure server;

retaining the images and the user information on the secure server such that the images and the user information retained on the secure server are each stored together and confined to a pre-selected storage plan;

providing online links to the images and the user information that is retained on the secure server such that the images and the user information that is retained on the secure server can be viewed while being stored;

retrieving the images and the user information stored in the secure server from a device other than the kiosk;

preventing downloading at the kiosk; and only accessing a username and password of the user through a computer and secure network, but not the kiosk;

wherein scanning images via a kiosk captures the images in digital format;

wherein said accepting user information from the user creates an account for the user and establishes user identification information;

wherein said creating an account for the user, the account having a storage plan, the account based upon said associating the user information with the images;

wherein said accepting payment from the user allows said uploading the images and the user information to a secure server, said uploading the images and the user information to a secure server based upon a storage plan chosen by the user;

wherein said preventing onlookers from viewing the user information and the images is achieved by using the display screen that can only be viewed by the user;

wherein said display screen is interactive;

wherein said reviewing the user information and the images is displayed on the display screen for final acceptance by the user;

wherein said uploading the images and the user information to a secure server is transferred in a secure format;

wherein said deleting the images and the user information from the kiosk erases all memory of the images and the user information from the kiosk after the user information and the images are successfully uploaded to the secure server;

wherein said retaining the images and the user information on the secure server is accessing the images and the user information via only methods other than email;

wherein said retrieving the images and the user information stored in the secure server is downloading via online access;

wherein said retrieving the images and the user information stored in the secure server is retrieving the images and the user through affirmative validation based on the personal identification information;

networking kiosks all configured to upload the images and the user information to the secure server;

collecting revenue from the user by the number of the images;

pressing a button corresponding to type of images the user intends to scan;

entering personal information on the display screen; and uploading the images to a remote location.

\* \* \* \* \*